United States Patent [19]
Olds et al.

[11] Patent Number: 5,597,533
[45] Date of Patent: Jan. 28, 1997

[54] APPARATUS FOR ANALYZING REFRIGERANT PROPERTIES

[75] Inventors: Daniel L. Olds; Sandra Sheehe, both of Bryan, Ohio

[73] Assignee: SPX Corporation, Muskegon, Mich.

[21] Appl. No.: 573,329

[22] Filed: Dec. 15, 1995

Related U.S. Application Data

[62] Division of Ser. No. 370,094, Jan. 9, 1995, Pat. No. 5,514,595.

[51] Int. Cl.$^6$ ................................................ G01N 1/42
[52] U.S. Cl. ..................... 422/68.1; 422/83; 422/82.09; 436/181; 62/130
[58] Field of Search .......................... 422/82.05, 82.09, 422/68.1, 83; 436/181, 164; 62/37, 125, 129, 130

[56] References Cited

U.S. PATENT DOCUMENTS

| | | |
|---|---|---|
| 4,304,102 | 12/1981 | Gray .................................... 62/195 |
| 4,436,641 | 3/1984 | Stelz et al. . |
| 4,649,711 | 3/1987 | Sibley ................................. 62/129 |
| 4,809,520 | 3/1989 | Manz et al. . |
| 4,862,699 | 9/1989 | Lounis . |
| 4,923,806 | 5/1990 | Klodowski . |
| 4,942,134 | 7/1990 | Winefordner et al. . |
| 5,062,273 | 11/1991 | Lee et al. . |
| 5,158,747 | 10/1992 | Manz et al. . |
| 5,174,124 | 12/1992 | Paige et al. . |
| 5,237,873 | 8/1993 | Eichenlaub . |
| 5,247,804 | 9/1993 | Paige et al. . |
| 5,255,527 | 10/1993 | Paige . |
| 5,295,360 | 3/1994 | Olds ..................................... 62/127 |
| 5,371,019 | 12/1994 | Manz ................................... 436/126 |
| 5,400,613 | 3/1995 | O'Neal ................................. 62/195 |

*Primary Examiner*—Jeffrey Snay
*Attorney, Agent, or Firm*—Barnes, Kisselle, Raisch, Choate, Whittemore & Hulbert

[57] ABSTRACT

One or more properties of a refrigerant sample, such as composition, purity or both composition and purity, are analyzed for purposes of refrigerant recovery and reuse by providing a refrigerant cell having a chamber for containing a refrigerant sample and a passage for connecting the chamber to a source of refrigerant in vapor phase. The sample chamber and passage are evacuated, and the chamber and at least a portion of the passage contiguous with the chamber are cooled until the temperature thereof reaches a predetermined temperature at or below ambient temperature. After the chamber and passage have been evacuated and cooled, the passage is connected to a source of refrigerant in vapor phase such that a refrigerant vapor sample is drawn into the chamber and condensed to liquid phase. After the cell chamber has been filled with a liquid refrigerant sample, one or more desired properties of the liquid refrigerant sample are measured or detected.

5 Claims, 2 Drawing Sheets

APPARATUS FOR ANALYZING REFRIGERANT PROPERTIES

This application is a division of application Ser. No. 08/370,094 filed Jan. 9, 1995, now U.S. Pat. No. 5,514,595.

The present invention is directed to refrigerant handling systems, and more particularly to a method and apparatus for analyzing properties of refrigerants such as refrigerant make-up or composition.

BACKGROUND AND OBJECTS OF THE INVENTION

It is now widely recognized and accepted that release into the atmosphere of chlorofluorocarbon(CFC)-based and hydrochlorofluorocarbon(HCFC)-based refrigerants has a deleterious effect on the ozone layer that surrounds the earth. Production of CFC-based and HCFC-based refrigerants is to be severely curtailed in the future, and the cost of refrigerant for service purposes is already increasing. It has therefore become standard practice in the refrigeration system service industry to recover, recycle and reuse the refrigerant in the refrigeration system under service, or to recover, store and reclaim the refrigerant for later reuse, rather than merely to vent such refrigerant into the atmosphere and replace with new refrigerant as had been common practice in the past. U.S. Pat. Nos. 4,768,347, 4,805,416 and 4,878,356, all assigned to the assignee hereof, disclose equipment for recovering, recycling and/or recharging refrigerant in a refrigeration system service environment.

As currently envisioned R-12 refrigerant is being replaced by different types of refrigerants in production of new refrigeration systems. For example, R-12 refrigerant is being replaced by R-134a refrigerant in the automotive industry—i.e., in automotive air conditioning systems. However, because these refrigerants and their associated lubricants are chemically incompatible with each other, inadvertent mixture of even small amounts of the different refrigerants can cause severe damage and early failure of the refrigeration system. It has been proposed to provide different service fittings on refrigeration equipment using different types of refrigerants, but the use of adapters and the like in the service industry may still result in inadvertent mixing of refrigerant/lubricant types, with consequent damage to the system under service and to the service equipment itself. A further complication arises with the use of intermediate refrigerants as substitutes for R-12 refrigerant, such as ternary blends made by DuPont. With severe curtailment of R-12 production in the future, it is anticipated that a significant number of refrigeration systems currently employing R-12 refrigerant may eventually be retrofitted with an intermediate substitute refrigerant. inadvertent mixing of refrigerants is considered to be an irreversible process, leading to disposal of the mixed refrigerant as hazardous waste.

The various types of refrigerants therefore need to be kept separate to protect the integrity of the service equipment, and to ensure proper integrity and performance of the refrigeration equipment under service. Use of an incorrect refrigerant or an undesired mixture of refrigerants can occur due to charging the incorrect refrigerant into the refrigeration equipment during installation or service, selective leakage or purging of one refrigerant component in a non-azeotropic refrigerant mixture, incomplete removal of the previous refrigerant in retrofitting equipment or clearing of the recovery/recycling service system, chemical reaction within the refrigerant such as during a high temperature mechanical failure or hermetic compressor burnout generating undesirable refrigerant by-products, or inadvertent mixing by recovery of refrigerant into an incorrect container or incorrect consolidation of recovered refrigerants into a larger container for shipment to a reclaim processing center.

In the past, refrigerant analysis has been accomplished by drawing a liquid refrigerant sample and sending the sample to a fully equipped refrigerant chemistry laboratory. An experienced chemist can remove some contaminants, such as oil, water and metallic particles, and then analyze the refrigerant using gas chromatography, mass spectroscopy or infrared spectroscopy. Air-Conditioning and Refrigeration Institute Standard 700-88 Specifications for Fluorocarbon Refrigerants specifies analysis of a liquid refrigerant sample. However, such laboratory analysis requires several hours or days to obtain, and is thus not suitable for use in the field. There is therefore a need in the refrigeration system service industry for a device that can be employed to test refrigerant in a storage container, or in a refrigeration system before performing service on the system, that is not restricted to any particular type of refrigerant or to automotive service applications, that is particularly well adapted to identify and distinguish between refrigerants of different types, that is inexpensive to manufacture and market, that is readily portable, that is rapid and efficient in operation, and/or that can be employed by relatively untrained service personnel.

U.S. Pat. No. 5,158,747, assigned to the assignee hereof, discloses a device for identifying and distinguishing between and among refrigerants of different types. The device includes a fixed volume for containing a sample of refrigerant. The refrigerant to be tested is selectively admitted into the volume in vapor phase, vapor pressure of refrigerant within the fixed volume is measured, and admission of refrigerant is terminated when the vapor pressure of refrigerant contained in the volume reaches a preselected level. A sensor and associated electronics are coupled to the sample-containing volume for determining type of refrigerant vapor as a function of one or more selected properties of the refrigerant, and indicating such refrigerant type to an operator. U.S. Pat. No. 5,295,360, also assigned to the assignee hereof, discloses an improved apparatus in which a thermistor provides a first electrical signal as a function of the combined effect of thermal conductivity and temperature of a refrigerant vapor sample in the sample-containing volume, and a temperature sensor provides a second electrical signal as a function of temperature of the refrigerant vapor sample essentially independent of thermal conductivity. Associated electronics determine type of refrigerant in the sample-containing volume as a function of the first and second electrical signals, and thus as a function of thermal conductivity of the refrigerant sample independent of sample temperature.

It has heretofore been proposed to employ near-infrared spectrophotometric analysis techniques for determining refrigerant make-up or composition. A liquid phase refrigerant sample is fed to a boiler, where the refrigerant sample is vaporized to separate refrigerant from oil and water. The refrigerant vapor is fed to a sample cell, where the vapor is condensed and subjected to near-infrared spectrophotometric analysis. Refrigerant make-up (i.e., refrigerant type or mixture of types) is determined by comparison of the near-infrared absorption spectra of the sample with pre-stored spectral data representative of known refrigerant types. Although the technique so proposed can provide an accurate indication of refrigerant type or types, improvements remain desirable. In particular, simplification is desirable to adapt the technique for use in the field. For example, the liquid phase refrigerant sample can contain up to twenty percent lubricant as well as dirt and metal particles, which can affect precision of the measurement process. The possible introduction of lubricant and particulates also necessitates cleaning of the test chamber or cell between uses.

U.S. application Ser. No. 08/160,224 now U.S. Pat. No. 5,371,019, also assigned to the assignee hereof, discloses a method and apparatus for analyzing one or more refrigerant properties by evacuating a refrigerant sample vessel or cell, drawing a sample of refrigerant vapor into the vessel, and condensing the refrigerant sample within the vessel for measuring and indicating one or more desired properties of the refrigerant sample in liquid phase. By drawing the sample refrigerant in vapor phase rather than liquid phase as theretofore proposed, the sample will be relatively free of lubricant, particulate and water contamination. The sample cell can be readily cleaned by simple evacuation in preparation for the next measurement cycle. The disclosed technique is also greatly simplified as compared with previous approaches by eliminating the necessity for boiling a liquid refrigerant sample. Although the technique so disclosed in the copending application advances the state of the art for the reasons indicated, further improvements remain desirable. In particular, difficulties are encountered, for differing refrigerants and differing levels of non-condensible contamination, in completely filling the chamber of the test vessel or cell with a liquid phase refrigerant sample. It is a general object of the present invention to provide a method and apparatus for analyzing refrigerant properties, in which the efficiency—i.e., the time duration and completeness—of the cell-filling operation is greatly enhanced as compared with the prior art.

SUMMARY OF THE INVENTION

One or more properties of a refrigerant sample, such as composition, purity or both composition and purity, are analyzed for purposes of refrigerant recovery and reuse in accordance with the present invention by providing a refrigerant sample vessel or cell having a chamber for containing a refrigerant sample and a passage for connecting the chamber to a source of refrigerant in vapor phase. The sample chamber and passage are evacuated, and the chamber and at least a portion of the passage contiguous with the chamber are cooled until the temperature thereof reaches a predetermined temperature at or below ambient temperature. After the chamber and passage have been evacuated and cooled, the passage is connected to a source of refrigerant in vapor phase, such that a refrigerant vapor sample is drawn into the chamber and condensed to liquid phase. After the cell chamber has been filled with a liquid refrigerant sample, one or more desired properties of the liquid refrigerant sample are measured or detected.

In the preferred embodiment of the invention, the refrigerant passage that is cooled with the sample chamber is provided with the sample chamber in a cell block. The passage is separate from and tangential to the sample chamber within the cell block, and has a length at least equal to diameter of the sample chamber. The cell block passage opens to the sample chamber at the lower portion of the chamber. Thus, the refrigerant is pre-cooled as it passes through the cell block passage to the sample chamber. A purge port is connected to the upper portion of the sample chamber for purging non-condensibles, which assists the filling process in situations of high concentration of air in the refrigerant sample, for example. The non-condensibles are purged through an orifice for controlling rate of purging. Light absorption in the mid- and far-infrared ranges may be employed to determine when the test chamber is full of liquid refrigerant.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF PREFERRED EMBODIMENT

Figure 1:
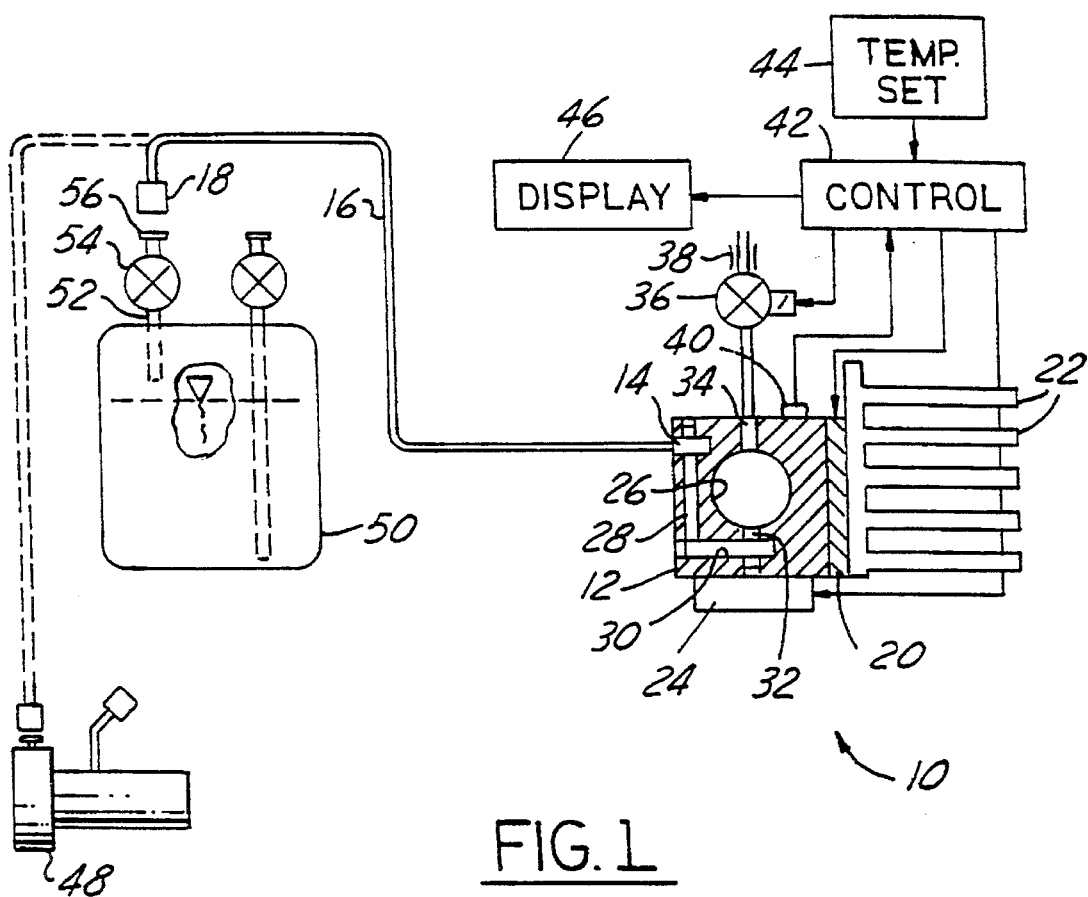
FIG. 1 is a schematic diagram of a refrigerant analysis apparatus in accordance with a presently preferred embodiment of the invention.

FIG. 1 illustrates an apparatus 10 for analyzing refrigerant in accordance with a presently preferred embodiment of the invention as comprising a vessel or cell block 12 for receiving and holding a refrigerant sample. Cell block 12 has an inlet port 14 connected by a conduit 16 to a coupling 18 for connection to a source of refrigerant vapor. Coupling 18 preferably comprises a self-sealing quick-disconnect coupling such as illustrated, for example, in U.S. Pat. Nos. 5,080,132 and 5,248,125. A thermoelectric heater/cooler 20 couples cell block 12 to a block of cooling fins 22. A sensor 24 is also coupled to cell block 12 for measuring one or more properties of refrigerant contained therewithin. Sensor 24 in the preferred embodiment of the invention comprises a source of near-infrared light and suitable filter/sensor units for illuminating refrigerant within cell block 12 and obtaining spectral photometric absorption data as a function of wavelength.

Within cell block 12 there is formed a central chamber or cavity 26 for holding a refrigerant test sample. A passage section 28 extends from cell block inlet port 14 along one side of the cell block tangential to chamber 26 to a second passage portion 30 that extends along a second side of cell block 12 again tangential to chamber 26 and at right angle to passage portion 28. Passage portion 30 connects with a chamber inlet 32 at the lower end of the chamber. A purge port 34 opens through cell block 12 from the upper end of chamber 26, and is connected through a solenoid valve 36 and an orifice 38 for purging chamber 12 to atmosphere. A temperature sensor 40 is operatively coupled to cell block 12 for providing an electrical signal as a function of temperature of chamber 26 and passage sections 28,30 within the cell block. Solenoid valve 36, temperature sensor 40 and thermoelectric heater/cooler 20 are all connected to an electronic control unit 42. Control 42 receives a temperature threshold input 44, and drives a display 46 for indicating one or more properties or parameters of the refrigerant under test, including temperature of cell block 12 from which refrigerant temperature is inferred, and one or more properties related to composition, purity or both composition and purity of the refrigerant within cell chamber 26.

In operation, sample cell 12 is first evacuated. This may be accomplished by connecting the vessel through coupling 18 to a vacuum pump 48, and then operating the vacuum pump to draw a vacuum (i.e., sub-atmospheric pressure) within the sample cell and conduit 16. Pressure within the sample cell preferably is reduced below at least 5,000 micrometers, and most preferably below 500 micrometers of mercury absolute, in order to ensure that the prior refrigerant sample and all contaminants are removed from within the sample cell. Vaporization and evacuation of the prior refrigerant sample may be assisted by energizing thermoelectric heater/cooler 22, using control 26, to vaporize the prior refrigerant sample.

Sample cell 12, including sample chamber 26 and refrigerant passage sections 28,30, are then pre-cooled by operation of thermoelectric heater/cooler 20, again using control 42, until temperature of the sample cell decreases to a preselected temperature at or below ambient temperature. This preselected temperature threshold is set at 44, and temperature of cell block 12 is monitored through sensor 40 and displayed at 46. For example, when inlet refrigerant vapor temperature is expected to be in the range of 55° to 120° F., the temperature threshold may be set at about 4.5° to 47° F.

After the temperature of cell block 12 has decreased to or below the temperature threshold set at 44, coupling 18 is connected to a source of test refrigerant in vapor phase. In FIG. 1, this source is illustrated as a refrigerant storage container 50 having a vapor port 52 connected through a manual valve 54 to a fitting 56 that mates with coupling 18. Coupling 18 may be preconnected to fitting 56, and valve 54 opened when the sample cell is precooled. In this configuration, apparatus 10 is used to analyze refrigerant within storage container 50. The apparatus may also be employed to analyze refrigerant within a refrigeration system under service, for example, by connecting coupling 18 to the system vapor port and opening the associated valve, if any.

Refrigerant vapor is drawn from within storage container 50 into test chamber 26 through conduit 16 and passage sections 28,30 by the reduced pressure within the cell chamber, passage and conduit resulting from the prior evacuation process and reduced temperature of the cell block. As the refrigerant vapor flows through passage sections 26,30 to chamber 26, the refrigerant vapor is pre-cooled in the cell block passage sections. As will be shown in connection with FIG. 2, this pre-cooling of the inlet refrigerant vapor greatly enhances the efficiency of the filling process. In situations where the filling process is slowed by a large quantity of non-condensibles such as air in the incoming refrigerant vapor, the filling process may be enhanced by opening valve 36 so as to purge the non-condensibles from sample chamber 26. Purging through orifice 38 helps control the rate of purging. An orifice size of 0.004 to 0.005 inches has been found suitable. Refrigerant flows through passage sections 28,30 into chamber 26 and is precooled by cell block 12.

Any suitable technique may be employed to determine when chamber 26 is full. For example, sensor 24 may be operated and monitored to indicate that chamber 26 is full when light is absorbed by the liquid refrigerant to a predetermined level at a specified wavelength. When near-infrared wavelengths are employed for refrigerant analysis, one or more wavelengths in the mid- or far-infrared regions may be employed for indicating a full chamber. The light will, of course, be absorbed more strongly by liquid phase refrigerant than by refrigerant vapor because of the increased number of light-absorbing refrigerant molecules.

With a liquid refrigerant sample now contained within cell chamber 26, infrared sensor 24 is operated by control 42 for measuring one or more properties of the refrigerant. Sensor 24 may be of any suitable conventional type for obtaining absorption data from the refrigerant sample, which data is then compared in control electronics 42 to prestored absorption data from known refrigerant types. Such absorption data comparisons shows not only the type of refrigerant within the vessel, but also whether the refrigerant sample is a mix of refrigerant types and whether the sample contains impurities (e.g., other refrigerants) that call for recycling or reclamation. Refrigerant type and purity so determined are indicated at display 46. Heater/cooler 20 preferably is operated by control 42 to maintain temperature within chamber 26 substantially constant during operation of sensor 24. Most or all of the refrigerant sample may then be removed from cell block 12 by operating heater/cooler 20 in a heating mode, which transfers a major portion of the refrigerant back to vessel 50. Any refrigerant or contaminates remaining in cell block 12 will be removed by subsequent connection to vacuum pump 48 during the next sample/measurement cycle. Sensors 24 other than infrared sensors may also be employed, such as an x-ray defraction sensor, a thermal conductivity sensor, a sensor for measuring dielectric properties of the refrigerant, a sensor for measuring molecular weight by ultrasonic techniques.

Figure 2:
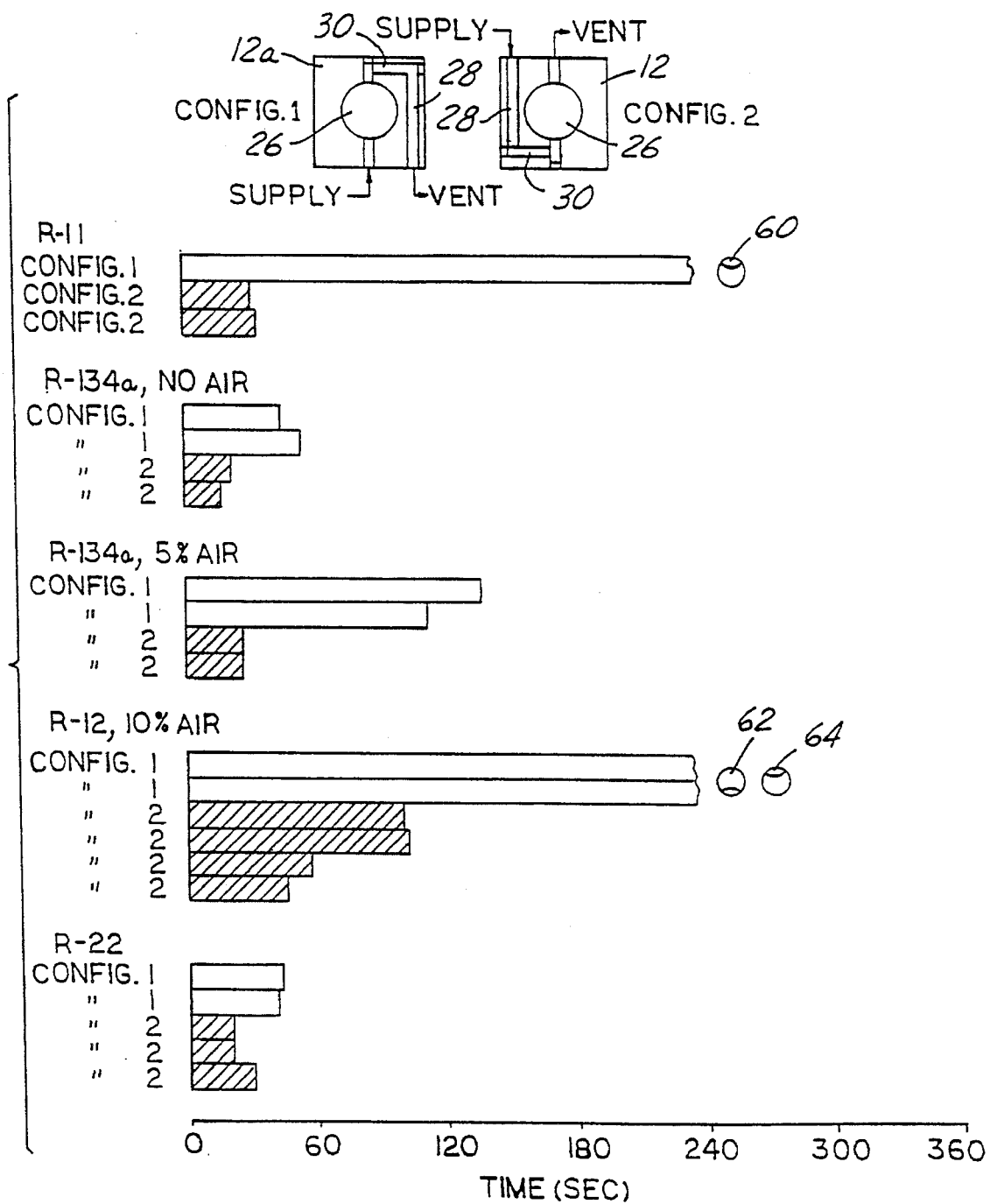
FIG. 2 is a graphic illustration of test results that demonstrate improved filling of the sample test chamber in accordance with the embodiment of the invention illustrated in FIG. 1.

FIG. 2 illustrates test results comparing operation of cell block 12 employing passage sections 28,30 as pre-cooling inlet passage sections as described in connection with FIG. 1 (configuration 2 in FIG. 2) with the same cell 12a (configuration 1) in which passage sections 28,30 are connected as part of the purge path and incoming refrigerant is supplied directly to chamber 26 without pre-cooling. The remainder of FIG. 2 consists of bar charts that illustrate filling efficiency (time and completeness) for various refrigerants, with or without entrained air. Both cell block 12 of configuration 2 and cell block 12a of configuration 1 were pre-cooled in identical test set-ups, and inlet refrigerant temperatures and pressures were otherwise identical in both cases. The only difference between the two test arrangements was disposition of cell block passage sections 28,30 as pre-cooling inlet passages in configuration 2, and not in configuration 1. Sample cell fill time was determined by visually observing the cell chamber and terminating the test when no air bubble remained in the chamber.

For R-11 refrigerant heated to a pressure of 8 psig, the configuration 1 cell arrangement had an air bubble 60 at the top of the cell chamber after sixty seconds. When it was them attempted to purge the cell through a 0.005 inch orifice, the cell could still not be filled because the refrigerant was purging as fast as it was flowing into the cell. However, using the configuration 2 cell arrangement under the same test conditions, the cell filled without purging in thirty-one seconds and thirty-four seconds in two test runs.

For R-134a with no entrained air, the fill time for configuration 1 of around forty-nine seconds was improved to around nineteen seconds in configuration 2 without purging. For R-134a with five percent air, the configuration 1 cell arrangement required one hundred fifteen to one hundred forty seconds to fill with continuous purging after the initial sixty seconds, whereas the configuration 2 cell arrangement was filled in twenty-seven to twenty-eight seconds without purging.

For R-12 refrigerant with ten percent entrained air, the configuration 1 cell arrangement would not fill even after purging. After one minute, the cell cross section 62 was still almost entirely filled with air, and a bubble 64 remained even after purging from three and one-half minutes to six minutes. The test was terminated after six minutes with the chamber still unfilled. With the configuration 2 cell arrangement, the cell chamber filled in one hundred three to one hundred five seconds with purging after sixty seconds. With purging for the first thirty-eight seconds, the cell fill time was reduced to fifty-eight seconds, and purging for the first thirty seconds produced a cell fill time of forty-six seconds.

For R-22 refrigerant with no entrained air, the fill time for the configuration 2 cell arrangement was twenty-one seconds, as compared with thirty-eight seconds for cell configuration 1 without purging. With purging during the initial thirty seconds, the configuration 2 to cell arrangement required thirty seconds to fill. R-502 refrigerant was also tested without entrained air, with results substantially the same as for the R-22 refrigerant as illustrated in FIG. 2.

Thus, pre-cooling the incoming refrigerant by routing through pre-cooled cell passage sections 28,30 in the temperature controlled test cell reduced the fill time by about fifty percent in situations where both cell configurations would fill—i.e., the R-134a with and without entrained air, and the R-22 and R-502 tests. In the R-11 and R-12 tests, the pre-cooling passages of the present invention allowed filling of the test cell, which would not otherwise fill.

We claim:

1. Apparatus for analyzing refrigerant that comprises:

a cell block having an internal chamber, a passage inlet, and passage means extending through said block tangential to said chamber and extending from said passage inlet to said chamber, means coupled to said cell block for cooling simultaneously said chamber and said passage means, means for selectively connecting said inlet of said cell block passage means to a vacuum pump for evacuating said chamber and said passage means, and to a source of refrigerant in vapor phase so as to draw a vapor phase refrigerant sample into said passage means and said chamber and condense the refrigerant sample to liquid phase within said chamber, and means operatively coupled to said cell block for detecting one or more properties of a condensed refrigerant sample in said chamber.

2. The apparatus set forth in claim 1 wherein the length of said passage means within said cell block is at least as great as the diameter of said chamber.

3. The apparatus set forth in claim 1 wherein said means for detecting refrigerant properties comprises means for subjecting the refrigerant sample in said chamber to mid-infrared or far-infrared spectrophotometric analysis.

4. The apparatus set forth in claim 1 further comprising means operatively coupled to said chamber for purging non-condensibles from said chamber.

5. The apparatus set forth in claim 4 wherein said purging means includes an orifice for controlling the rate of purging of non-condensibles.

\* \* \* \* \*